United States Patent [19]
Zhu

[11] Patent Number: 5,432,096
[45] Date of Patent: Jul. 11, 1995

[54] SIMULTANEOUS MULTIPLE, SINGLE WAVELENGTH ELECTROMAGNETIC WAVE ENERGY ABSORBTION DETECTION AND QUANTIFYING SPECTROPHOTOMETRIC SYSTEM, AND METHOD OF USE

[75] Inventor: Jianzhong Zhu, Omaha, Nebr.

[73] Assignee: CETAC Technologies Inc., Omaha, Nebr.

[21] Appl. No.: 149,297

[22] Filed: Dec. 20, 1993

[51] Int. Cl.⁶ .............................................. G01N 21/27
[52] U.S. Cl. .................................... 436/171; 436/164; 436/94; 422/82.09; 356/73
[58] Field of Search ................ 422/82.05, 82.09; 436/94, 164, 172, 180, 171, 86, 52; 356/73, 436

[56] References Cited

U.S. PATENT DOCUMENTS

| | | |
|---|---|---|
| 4,294,802 | 10/1981 | Johansson . |
| 4,312,945 | 1/1982 | Yamada et al. ........................ 435/26 |
| 4,398,894 | 8/1983 | Yamamoto . |
| 4,399,099 | 8/1983 | Buckles . |
| 4,582,687 | 4/1986 | Karoishi et al. . |
| 4,610,544 | 9/1986 | Riley . |
| 4,640,821 | 2/1987 | Mody et al. . |
| 4,685,801 | 8/1987 | Minekane .......................... 422/82.09 |
| 4,775,637 | 10/1988 | Sutherland et al. . |
| 4,810,658 | 3/1989 | Shanks . |
| 4,818,710 | 4/1989 | Sutherland et al. . |

Primary Examiner—Jeffrey R. Snay
Attorney, Agent, or Firm—James D. Welch

[57] ABSTRACT

Spectrophotometric sample analysis systems, and methods of their use, capable of "simultaneously" detecting, quantifying, displaying and/or recording energy absorption factors, and ratios of various energy absorbtion factors, regarding a multiplicity of single frequency electromagnetic waves in a beam of multiple single wavelength electromagnetic waves which is caused to pass through a sample analyte containing sample solution, are disclosed.

20 Claims, 2 Drawing Sheets

SIMULTANEOUS MULTIPLE, SINGLE WAVELENGTH ELECTROMAGNETIC WAVE ENERGY ABSORBTION DETECTION AND QUANTIFYING SPECTROPHOTOMETRIC SYSTEM, AND METHOD OF USE

TECHNICAL FIELD

The present invention relates to sample analysis systems for use in detecting and quantifying analytes present in sample solutions. More particularly, the present invention pertains to spectrophotometric systems, and methods of use, for detecting and quantifying analytes in a sample solution, (typically present in quantities on the order of a few microliters or less), by a method which simultaneously determines absorbtion of energy from a multiplicity of single wavelength electromagnetic waves, in a beam of multiple single wavelength electromagnetic waves which is caused to pass through a sample solution.

BACKGROUND

Typical spectrophotometric sample analysis systems require that multiple, single wavelength electromagnetic waves be applied to a sample solution sequentially during an analyte detection and quantification procedure to, for instance, detect and quantify multiple analytes or an analyte and contaminants present therein. That is multiple, single wavelength electromagnetic waves in a beam of electromagnetic waves can not be simultaneously caused to pass through a sample solution and the energy absorbed by said sample solution from each single wavelength electromagnetic wave simultaneously detected, analyzed, displayed and/or recorded. A user of typical spectralphotometric systems must then typically change monochrometers and filters in a typical spectrophotometric system between analysis steps to provide sequentially, the electromagnetic wave single wavelengths required. Use of such systems is thus tedious and time consuming and the results provided thereby are prone to error. It is emphasised that a system which would allow immediate simultaneous analysis, display and/or recording of energy absorbed from a multiplicity of single wavelength electromagnetic waves which are caused to simultaneously pass through a sample as a beam of electromagnetic waves, would greatly increase convenience of use and improve accuracy of achieved analysis results.

In addition, most sample analysis systems have limited capability regarding detecting and quantifying analytes dissolved in small volume sample solutions, (on the order of a few microliters or less), and small sample solution volumes must often be diluted to provide sample solution volumes sufficiently large to fill sample retaining volumes present therein. Of course, dilution reduces the concentration of the analytes in a sample solution, and said reduction of analyte concentration makes it more difficult for the sample analysis system to detect and quantify said analytes.

Continuing, while the present invention is not limited to use with nucleic acids, (eg. DNA, RNA), and proteins, said sample analytes are at times particularly difficult to obtain in solution volumes greater than a few microliters. The following discussion uses nucleic acid and proteins as an example to further describe the above identified problem.

There are two basic approaches to detecting and quantifying nucleic acids in a sample:
1. Ethidium Bromide Fluorescence, applicable to DNA, and
2. Spectrophotometry, applicable to DNA & RNA.

It is mentioned in passing that if the sample analyte is DNA, an approach, as indicated, to quantifying the amount present is by use of a technique which uses Ethidium Bromide. Said technique is applicable to small volumes of sample. Said technique provides that double strand DNA be subjected to treatment with Ethidium Bromide, which Ethidium Bromide interacts with the double stranded DNA to become intercalated therein. When Ultraviolet light is then caused to illuminate the DNA-Ethidium Bromide combination, fluorescence occurs. The amount of fluorescence is directly proportional to the amount of DNA present. As alluded to, however, this technique is not applicable to single stranded RNA.

The spectrophotometric sample analyte detection and quantification technique as applied to nucleic acids requires measurement of the amount of energy absorbtion from two single wavelength, (eg. two-hundred-sixty (260) and two-hundred-eighty (280) nanometers), electromagnetic waves which are caused to pass through a volume of sample solution which contains nucleic acid analytes. Energy absorbtion at two-hundred-sixty (260) nanometers is proportional to the quantity of nucleic acids present and that at two-hundred-eighty (280) nanometers is an indication of the presence of protein or phenol contaminants, for instance. In the absence of protein or phenol the ratio:

$$(\text{Absorbtion at 260 nm})/(\text{Absorbtion at 280 nm})$$

is typically not significantly lower than:
1. 1.8 for DNA, and
2. 2.0 for RNA.

If a ratio value lower than indicated is obtained, energy absorbtion interference at two-hundred-sixty (260) nanometers is indicated and the nucleic acid purity of the sample under analysis is questionable.

The above discussion provides insight to the fact that, particularly in the area of where nucleic acids and proteins are the analytes present in a sample solution, a need exists for a sample analysis system, preferable a spectrophotometric sample analysis system, which can provide sample analyte quantification analysis, especially when only a few microliters or less of relatively concentrated analyte containing sample solution are available. It is noted, however, that sample analytes other than nucleic acids and proteins are often available in only very small solution volumes as well, and that spectrophotometric analysis techniques of determining the quantity of sample analyte present therein can be equally applicable thereto. Typically, wavelengths other than two-hundred-sixty (260) and two-hundred-eighty (280) nanometers are used when sample anlaytes other than nucleic acids are present, but the spectrophotometric sample analysis technique is unchanged. That is, the simultaneous determination of the energy absorbtion from each of two or more single wavelength electromagnetic waves, in a beam of electromagnetic waves, as it is passed through a sample analyte containing solution, is identifying of the quantity of certain sample analytes present therein.

A Search for Patents which describe spectrophotometric sample solution analysis systems for use in analysis of analytes in microliter volumes of sample solutions provided no Patents directly focused on analysis of small volumes of nucleic acid or protein solutions. Patents which describe the use of sample flow cell systems, a Patent which describes a small volume (eg. 1 microliter), pumping system and Patents which describe measurement of absorbtion of one or more signals issuing from waveguides in which are present analytes, however, were identified.

A Patent to Johansson, U.S. Pat. No. 4,294,802 describes a system which is capable of feeding a number of small volume (eg. one (1) microliter), sample solution boluses, simultaneously through a number of parallel flexible hoses.

A Patent to Riley, U.S. Pat. No. 4,610,544 describes a system for entering reagent and sample into a flow channel of preferably not greater than one (1) milimeter internal diameter. A single peristalic pump is used to draw reagent and sample into separate arms of the flow channel, which merge. A carrier liquid is sequentially drawn into the flow channel to carry along a discrete liquid slug of mixed reagent and sample. The flow cell is generally sufficiently long to allow reagent and sample to react with one another prior to entering an analytical station, such as a colorimiter or spectrophotometer. The Background Section in Riley describes prior discrete analyzers in which a sample is placed in an individual container during analysis. In addition, systems which mix, and retain for a designated time, sample and reagent in a chamber and then pass said mixture to a measurement sell such as a photometric measurement system are alluded to. Systems in which multiple samples are caused to flow sequentially along a flow channel with or without intervening separators such as slugs of air are also mentioned. Flow injection systems in which the carrier medium is the reagent and into which is injected precisely measured amounts of sample by syringe through a septum, or a rotary valve are also mentioned.

A Patent to Kuroishi, U.S. Pat. No. 4,582,687 describes a system for performing rate assay analysis. Sample and reagent are introduced into a stream of carrier liquid and transferred through a series of flow cells. Said series of flow cells are positioned such that a single beam of light simultaneously passes through each. The reagent and sample enters a first flow cell early in the reaction process between said reagent and sample and the absorbtion of the light beam thereby is monitored. A delay line, (eg. a long coil reaction tube), carries the reacting reagent and sample into the next flow cell, after all such reagent and sample has left the first flow cell, and again the absorbtion of the light beam is monitored. The difference in absorbtion factors is related to the rate of the reaction between the reagent and the sample. The period of time between the reagent and sample entering the first and a subsequent flow cell is determined by the length of the delay line.

A Patent to Yamamoto, U.S. Pat. No. 4,398,894 describes a system for quantitatively determining the degree of agglutination of particles. A liquid which contains agglutinated clots is made to slowly transfer through a small tube. In the course of said transfer agglutinated clots and nonagglutinated particles separate from one another in the liquid. The difference between optical properties of the leading edge, (ie. agglutinated layer), and trailing edge, (ie. non-agglutinated particles), of a transferring agglutinated clot and surrounding liquid provides a quantification of the degree of agglutination present. Optical properties are detected by photometric means at multiple locations along the small tube.

A Patent to Sutherland et al., U.S. Pat. No. 4,775,637 describes an immunoassay apparatus having two waveguides. One waveguide has its internal surface coated with a reactant specific to a component for which analysis is desired. The other waveguide does not have such a coating present. Dual beams are generated from a monochromator and one of said beams is caused to pass through one of said dual waveguides, and the other of said beams is caused to pass through the other of said dual waveguides. Measurement of relative absorbtion of the two beams provides information regarding the presence of a component which reacts with the reactant present on the internal surface of one of the waveguides. Simultaneous monitoring of two signals is thus an important aspect of the operation of the invention. However, use of two different wavelengths is not taught. A second Patent to Sutherland et al., U.S. Pat. No. 4,818,710 does suggest the use of two or more wavelengths, but requires that one or more coatings of reactants specific to species to be analyzed be present. A light signal carried by a waveguide undergoes interaction with a bulk analyte and leads to development of a first signal. Simultaneously said light signal interacts with a layer of complex which results from the reaction of one or more specific reactants with one or more species to be analyzed, leading to development of a second, (or more) signal. When a second wavelength is used in the light signal, the waveguide is coated with different specific reactants at different locations along it length. The two, or more, different wavelength signals developed are separated for analysis by band-pass, dichromatic beam splitters etc. Sample entry through a flow cell is taught. Signals to be analyzed can be developed by absorbtion, scattering or the generation of fluorescence.

A Patent to Buckles, U.S. Pat. No. 4,399,099 describes a system which employs an energy transmissive core and employs one or more sheaths which selectively absorb, react with, and/or filter an analyte or product of an analyte. The passage of energy through the energy transmissive core is modified by reason of events which occur in one or more of the sheaths. If no sheath is present, events which occur in an ambient fluid serve as energy passage modifiers. The resulting modification of transmitted energy is monitored and serves as a measure of analyte. The energy may be present in electromagnetic form, electrical or sonic form. The Buckles teachings are that two or more such systems can be used simultaneously to simultaneously measure more than one analyte.

A Patent to Shanks et al., U.S. Pat. No. 4,810,658 describes a method for analyzing small liquid samples optically to discriminate sample material which is bound to a solid surface from sample material which remains free in solution. Light is entered into a transparent solid optical waveguide surface, which surface is perpendicular to the optical axis of said waveguide and to which surface is bound sample material. Light emerging from the end of the waveguide within a certain angle with respect to the optical axis of said waveguide is measured. The emerging light provides the desired information. While the limiting sample solution volume which can be analyzed by the system is not specifically designated, mention of a Patent G.B. No. 2,090,659 in the Background Section of the Patent indicates that a sample size of more than ten (10) microliters is required.

From the above it can be concluded that while prior Patents teach systems and methods which use flow cells, pump small volumes, (eg. one (1) microliter), of sample solution, simultaneously utilize multiple light beams and light beams comprised of more than one wavelength to provide sample analysis; a need still exists for simple to use Spectrophotometric sample analysis system which can "simultaneously" quantify the amount of nucleic acids, proteins and/or other sample analytes which are present in a sample solution, when the sample solution volume available for analysis is on the order of a few microliters or less. Said system should have the capability to analyze a small volume of sample solution for the presence and quantity of many sample analytes essentially simultaneously, and instantaneously display and/or record said analysis results.

DISCLOSURE OF THE INVENTION

The need identified in the Background Section of this Disclosure is met by the system and method of the present spectrophotometric sample analysis system invention.

In a first embodiment, the present invention comprises a system of one or more sample flow cells each of which contains a channel, (eg. typically on the order of a few microliters or less in volume), and means to cause a continuous flow of carrier fluid therethrough during use. In addition, a means by which a single or multiple sample analyte containing bolus of sample solution can be entered to a sample flow cell, ahead of said channel, into the continuous flow of carrier fluid, is also present, as are means by which a multiple single wavelength electromagnetic wave beam can be caused to pass through the one or more sample analyte containing bolus of sample solution as it passes through said channel of the sample flow cell. It is specifically mentioned that the volume of the one or more sample analyte containing bolus of sample solution is preferably equal to, or just greater than the channel volume of the sample flow cell so that during use said one or more sample analyte containing bolus of sample solution completely fills said channel when the multiple single wavelength electromagnetic wave beam is caused to pass therethrough.

In a modified embodiment of the present invention a cuvette with a channel, (eg. typically of a microliter volume), therethrough is provided analyte containing sample solution by way of a pipet, for instance. Means by which a multiple single wavelength electromagnetic wave beam can be caused to pass through a one or more sample analyte containing sample solution entered into said cuvette are, again, also present.

The present invention also comprises means to determine the amount of energy absorbtion which occurs in various single wavelength electromagnetic waves in the multiple single wavelength electromagnetic wave beam passed through the one or more sample analyte containing sample solution as it passes through a sample flow cell channel or rests in a cuvette channel. Said means include the use of beam splitters and filters which selectively split an electromagnetic wave beam into multiple such beams and pass the resulting multiple electromagnetic wave beams to one or another means for determining energy absorbtion. Means for immediately displaying energy absorbtion factors are also present. Typically a peak energy absorbtion factor retaining means which can feed to display or memory means will be present as well. This is especially relevant to the first embodiment of the present invention because the amount of a single wavelength in a multiple single wavelength electromagnetic wave beam absorbed by one or more sample analytes in a sample analyte containing solution bolus as it passes through the channel of the sample flow cell will be greatest when the bolus of sample analyte containing solution optimumly fills the volume of said channel. Electromagnetic wave beam energy absorbtion will then, typically, rise to a peak and then decline as a bolus of sample analyte containing solution enters into the present invention and passes through and out of the channel of a sample flow cell of the first embodiment of the present invention.

The first embodiment of the present invention typically uses pumping means to cause the continuous flow of carrier fluid through the channel of the sample flow cell, and provides a sample analyte containing solution access to said continuous flow of carrier fluid, ahead of said channel, through, typically, a self resealing septum, by means of a small volume, (eg. ten (10) microliters), hypodermic needle and syringe-like system. (Note that other sample analyte containing sample solution entry means are also possible and their presence and use is within the scope of the present invention). In use a microliter or so bolus, (typically selected to be equal to or to just exceed the volume of the channel of the sample flow cell of the present invention, if possible in view of the amount of sample available), of a one or more sample analyte containing sample solution will be placed into the small volume (eg. ten (10) microliter), hypodermic needle and syringe-like system, the needle thereof will then be inserted through the typically self resealing septum, into the continuous flow of carrier fluid, and the microliter or so bolus of the one or more sample analyte containing sample solution will be injected into the continuous flow of carrier fluid. The microliter or so bolus of the one or more sample analyte containing sample solution will, under the influence of the continuous flow of carrier fluid into which it is entered, flow through the channel of the sample flow cell. Simultaneously, a multiple single wavelength electromagnetic wave beam will be passed therethrough. One or more single wavelength electromagnetic waves in the multiple single wavelength electromagnetic wave beam, as mentioned, can be split from the initial multiple single wavelength electromagnetic wave beam by passage through wave splitters and filters positioned past the channel, for instance.

In practice a multiplicity of sample flow cells can be sequentially interconnected so that a microliter or so volume bolus of sample analyte containing sample solution is carried through the channels of each prior to disposal thereof. Said arrangement increases the number of single wavelength electromagnetic waves for which energy absorbtion data can be obtained, while utilizing only one bolus of sample solution.

As alluded to above, when the modified embodiment of the present invention is utilized, sample solution is typically entered to the cuvette channel by way of a pipet and it is to be understood that said sample solution remains essentially stationary therein during detection and quantization of analytes contained therein.

The system of the present invention is typically contained in a desk-top sized containment, (eg. on the order of twelve (12) inches square on a side and six (6) inches in height). Controls, continuous fluid flow fluid entry and exit ports, (when present), sample analyte containing solution entry port and display means are arranged thereon to allow easy use thereof.

The present invention will be better understood by reference to the Detailed Description Section of this Disclosure in conjunction with the Drawings.

SUMMARY OF THE INVENTION

Typical existing spectrophotometry sample analysis systems are not easy to use, requiring that a user sequentially obtain energy absorbtion data for multiple single wavelength electromagnetic wave beams, rather than provide for simultaneous energy absorbtion data acquisition for more than one such single wavelength electromagnetic wave in a beam of a multiplicity of single wavelength electromagnetic waves.

In addition, the inability of most sample analysis systems to detect and quantify sample analytes present in solution volumes of a few microliters or less is well known. The problem is particularly pronounced when sample analytes are nucleic acids, (eg. DNA and RNA) and/or proteins and where phenol or other contaminants might be present.

Where DNA is the analyte of interest microliter volumes of sample analyte containing solution can be investigated by fluorescence of ethidium bromide which is caused to become intercalated into the double stranded DNA molecule, typically by a mixing process. However, this technique is not applicable when single stranded RNA or protein or other analyte is to be analyzed.

Spectrophotometric analysis is an approach to sample analysis which is applicable whether DNA or RNA or another sample analyte is present. Briefly, known sample analysis systems which utilize said technique cause a sequential series of single wavelength electromagnetic wave beams to be passed through a sample analyte containing solution and the energy absorbed from each single wavelength electromagnetic wave beam as it is passed therethrough is displayed and/or stored. Said energy absorbtion is proportional to the quantity of a sample analyte present in the sample solution which absorbs electromagnetic wave energy of the wavelength present. No known spectralphotometric system, however, provides for "simultaneous" display and/or recording of energy absorbtion factors for a multiplicity of single wavelength electromagnetic waves in a beam of a multiplicity of single wavelength electromagnetic waves. Also, as mentioned above, many existing analysis systems which use this technique require that sample analyte containing solution volumes on the order of hundreds of microliters be available. That is, the internal volumes of sample containing channels thereof are on the order of hundreds microliters. As a result, when smaller sample analyte containing solution volumes are to be investigated, additional solvent must be added thereto. This of course causes dilution of the sample analytes present, and makes their detection and quantification more difficult, and at times impossible.

A system which would allow application of the Spectrophotometric technique to sample analyte analysis, and which could "simultaneously" apply and analyze energy absorbtion factors from a multiplicity of single wavelength electromagnetic waves present in a multiple single wavelength electromagnetic wave beam, would therefore be of great utility. This would be especially true if the system were applicable to the analysis of sample analyte containing solution volumes of a few microliters or less.

The present invention provides such a system and, in its first embodiment is comprised of a sample flow cell with a channel therein through which a continuous flow of carrier fluid is caused to flow during use. Said first embodiment of the present invention allows entry of a microliter or so bolus of sample analyte containing sample solution into the continuous of carrier fluid, ahead of said channel in the sample flow cell, so the microliter or so bolus of sample analyte containing solution is caused to flow into, through and out of said channel under the influence of the continuous flow of carrier fluid. The present invention also provides means for developing and directing a multiple single wavelength electromagnetic wave beam so that it is caused to pass through said microliter or so bolus of sample analyte containing sample solution as it passes into, through and out of said channel of the sample flow cell. The present invention also provides means for simultaneously detecting and immediately displaying and/or recording the amount of energy absorbed from one or more single wavelength electromagnetic waves present in the multiple single electromagnetic wavelength beam as it is caused to pass through said microliter or so bolus of sample analyte containing sample solution, as said microliter or so bolus of sample analyte containing sample solution travels into, through and out of said channel. The present invention allows immediate display of instantaneous and peak energy absorbtion factors for multiple single wavelength electromagnetic waves, as well as ratios of more than one such energy absorbtion factor. Typically wave splitters and filters are used to direct different wavelength electromagnetic waves into different energy absorbtion detectors.

The first embodiment of the present invention typically provides that sample analyte containing sample solution is entered into the continuous flow of carrier fluid in the sample flow cell, ahead of the channel therein, by means of a needle which is a part of a needle and hypodermic syringe-like system, although the presence and use of other small volume sample analyte containing sample solution entry means are within the scope of the present invention. Said needle is typically caused to pierce a typically self resealing septum and enter the continuous flow of carrier fluid which is present therebelow. Said typically self resealing septum serves as a continuous barrier between the internal volume of the channel of the sample flow cell and the external environment. Continuing, when so positioned the needle and hypodermic syringe-like system is operated to inject a microliter or so bolus of sample analyte containing sample solution, ahead of the channel. When the needle is removed from the typically self resealing septum, it reseals to again form a continuous barrier between the internal volume of the volume sample flow cell channel and the external environment. Typically the volume of the sample analyte containing sample solution, bolus will be equal to or just larger than the volume of the sample flow cell channel.

A modified embodiment of the present invention provides a channel containing cuvette, into which channel a small volume of analyte containing sample solution can be entered, typically by a pipet. Said small volume sample solution remains stationary in said cuvette channel during simultaneous application of a multiple single wavelength electromagnetic wave beam. During use, energy absorbtion from selected single wavelength electromagnetic waves, and possibly ratios thereof, are simultaneously displayed and/or recorded.

It is noted that a multiple single frequency electromagnetic wave beam can be provided via a phosphor plate upon which a source of multiple wavelength electromagnetic radiation is caused to impinge. Phosphor plates can be selected to provide desired wavelengths.

The present invention then provides a system and method of use which is applicable to "simultaneous" detection and quantification of multiple sample analytes, or a sample analyte and contaminants, which are present in a sample solution volume of a few microliters or less. When nucleic acids and/or proteins are the analytes of interest, a multiple single wavelength electromagnetic wave beam comprised of two-hundred-sixty (260) and two-hundred-eighty (280) nanometers wavelength electromagnetic waves will typically be utilized, and energy absorbtion from each will be analyzed. Other sample analytes, however, can be analyzed by use of other wavelength components in a multiple single wavelength electromagnetic wave beam.

It is therefore a purpose of the present invention to provide a Spectrophotometric system which can apply a multiple single wavelength electromagnetic wave beam to an analyte containing solution and "simultaneously" determine, display and/or store the energy absorbed from selected single wavelength electromagnetic waves therein as it is caused to pass through said analyte containing solution.

It is another purpose of the present, invention to provide a Spectrophotometric sample analysis system which can simultaneously detect and quantify multiple analytes present in a sample solution.

It is yet another purpose of the present invention to provide a Spectrophotometric sample analysis system which can detect and quantify sample analytes present in sample solution volumes of a few microliters or less.

It is still yet another purpose of the present invention to provide a Spectrophotometric sample analysis system which can immediately display single wavelength electromagnetic wave energy absorbtion factors, and/or ratios of more than one such energy absorbtion factor, for one or more single wavelength electromagnetic waves as said single wavelength electromagnetic waves are "simultaneously" passed through sample analyte containing sample solution.

It is another purpose of the present invention to provide a spectrophotometric sample analysis system which is housed in an encasement which is sized to easily set on top of a small desk.

It is another purpose of the present invention to provide a spectrophotometry sample analysis system which is easy to use and which provides a user immediate sample analysis results.

DETAILED DESCRIPTION

Figure 1:
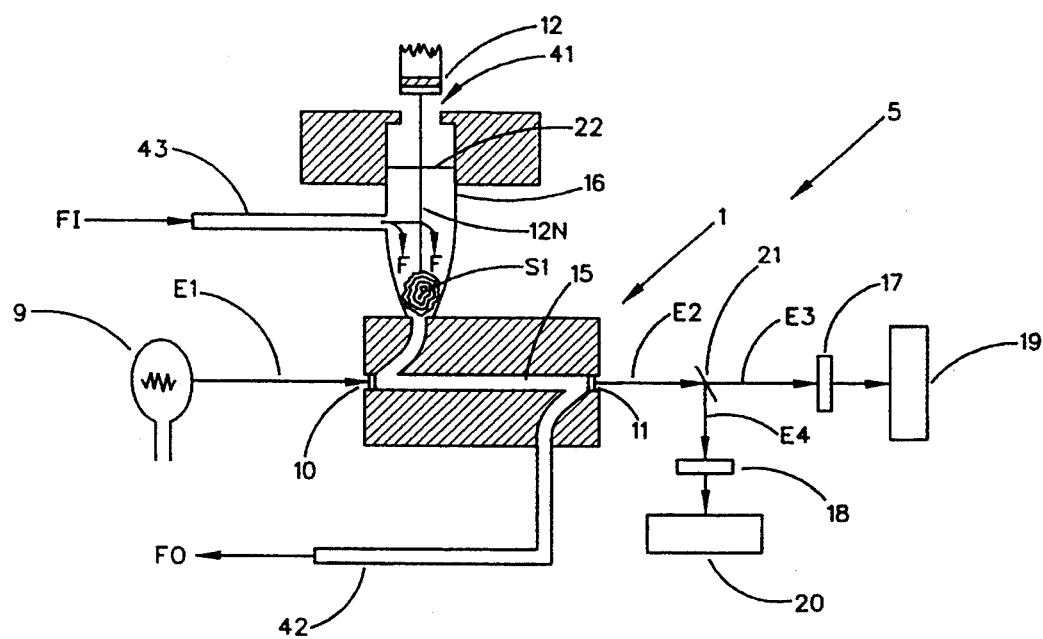
FIG. 1 shows a diagramatic view of the basic elements of the first embodiment of the present spectrophotometric sample analysis system utilizing flow cell sample entry means for use in analysis of microliter sample volumes.

Turning now to FIG. 1, there is shown the basic system of a first embodiment of the present invention (5). A sample flow cell (1) is shown with a microliter volume channel (15) therein. A source of a multiple single wavelength electromagnetic wave beam (9) is shown providing a multiple single wavelength electromagnetic wave beam (El) to sample flow cell (1) at input aperture (10). Said multiple single wavelength electromagnetic wave beam (1) is oriented so as to pass through the microliter volume channel (15) of sample flow cell (1) and emerge from output aperture (11) where it is designated as (E2). A beam splitter (21) intercepts multiple single wavelength electromagnetic wave beam (E2) and provide two electromagnetic wave beams (E3) and (E4). Said electromagnetic wave beams (E3) and (E4) can be of multiple single wavelength composition, or said beam splitter (21) can be of the type which selects single wavelengths to pass on in each said electromagnetic wave beam (E3) and (E4). Filters (17) and (18) are shown in the paths of electromagnetic wave beams (E3) and (E4) and if present serve to further restrict the wavelengths in electromagnetic wave beams (E3) and (E4) applied to spectrophotometric detectors (19) and (20) respectively. Said filters (17) and (18) are more required if the beam splitter (21) passes multiple single wavelength electromagnetic wave as beams (E3) and (E4), but less necessary if beam splitter (21) selects single wavelength electromagnetic wave to pass along as beams (E3) and (E4). Note that Part No. SU-25, available from Optics For Research Inc., in Caldwell, N.J. is exemplary of beam splitters which might be utilized in the present invention. It is to be noted that the beam splitter arrangement just described is considered to be a particularly relevant aspect of the present invention in any embodiment thereof. It is because of its presence that energy absorbtion factors for multiple single frequency electromagnetic waves in a beam of a multiplicity of electromagnetic waves which is passed through an analyte containing sample solution, can be "simultaneously" provided, displayed and/or stored.

During use a flow of carrier fluid (F) is entered to chamber (16) as (FI) through input port (43). Carrier fluid (F) flows through the microliter volume channel (15) of sample flow cell (1) and exits as (FO) at output port (42), typically under the influence of pumping means. A sample solution to be analyzed is shown as entered into a hypodermic needle-syringe type system (12) and the needle (12N) thereof is placed through sample input port (41) and typically self resealing septum (22) to position the end of said needle (12N) in the flow of carrier fluid (F). Said sample solution is then injected into the flow of carrier fluid (F) as microliter or so volume bolus (S1). Detectors (19) and (20) monitor the change in energy absorbtion of the electromagnetic wave beams (E3) and (E4) as sample bolus (S1) passes through small (eg. microliter), internal volume channel (15) in sample flow cell (1). Said change in energy intensity, via absorbtion in the bolus of sample solution as it passes through the small volume channel (15), provides information as to the presence and quantity of sample analytes present in sample bolus (S1) which absorb electromagnetic energy of the wavelengths being detected.

Figure 2:
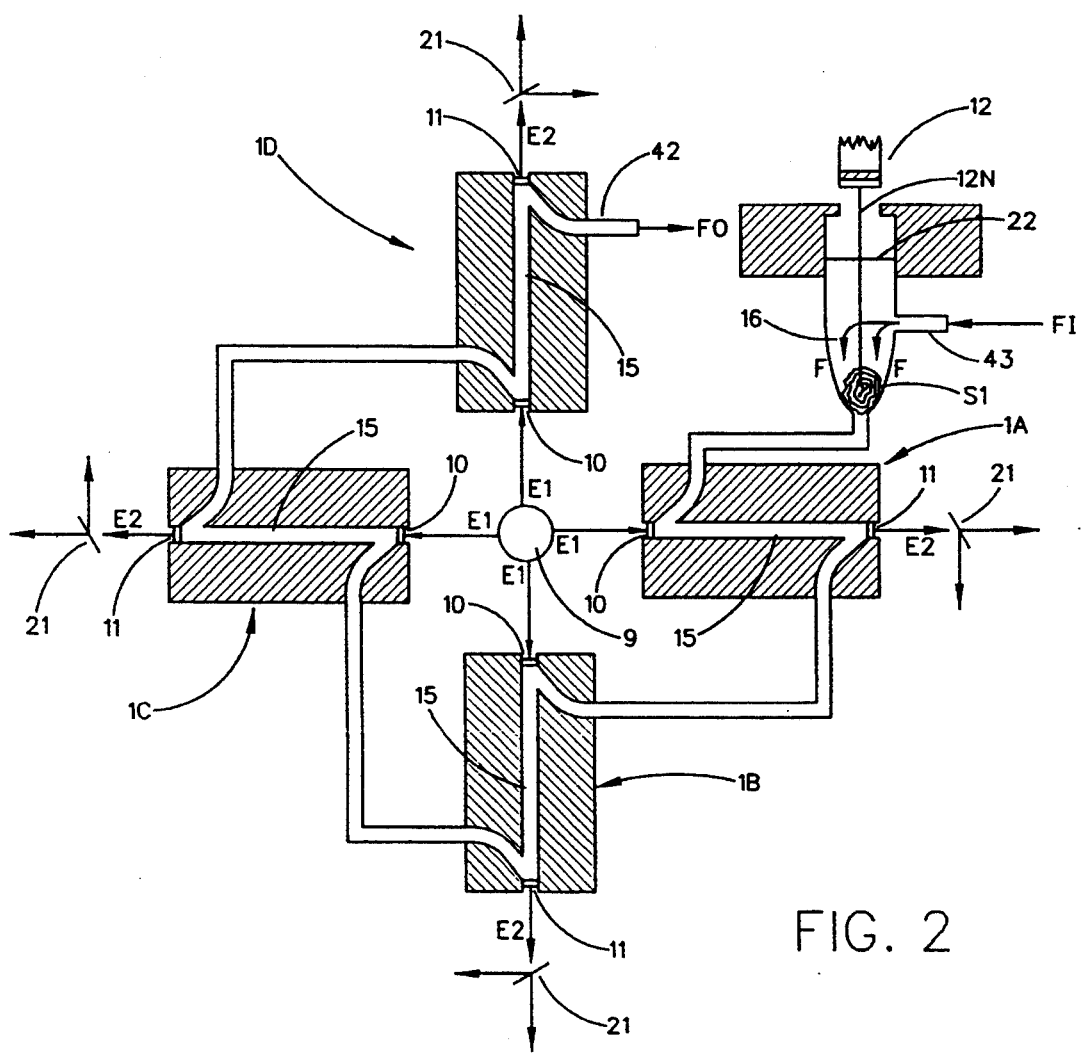
FIG. 2 shows a diagramatic view of a seriesed combination of four small internal channel volume sample flow cells of the first embodiment of the present invention.

Turning now to FIG. 2, there is shown a seriesed combination of four sample flow cells (1A), (1B), (1C) and (1D) with small volume channels (15). As in the system of FIG. 1, a carrier fluid flow (F) is input to input port (43) as (FI). Said carrier fluid flow through small volume channels (15) of sample flow cells (1A), (1B), (1C) and (1D) prior to exiting as (FO) at output port (42). Multiple single wavelength electromagnetic wave beams (El) are shown leaving source (9) and impinging upon input apertures (10) of the various sample flow cells. Multiple single wavelength electromagnetic wave beams (E2) leave output apertures (11) and impinge onto wave splitters (21). As described with respect to FIG. 1, electromagnetic wave beams (E3) and (E4), can be multiple wavelength or single wavelength and might pass through filters prior to entering detectors analogous to filters (17) and (18) and detectors (19) and (20) in FIG. 1. The system of FIG. 2, it will be appreciated, allows a user to investigate a microliter volume sample solution via eight (8) different wavelength electromagnetic wave beams. Additional sample flow cells (1) could also be incorporated into the scheme of Fig. two to further increase the analysis capability.

Figure 4:
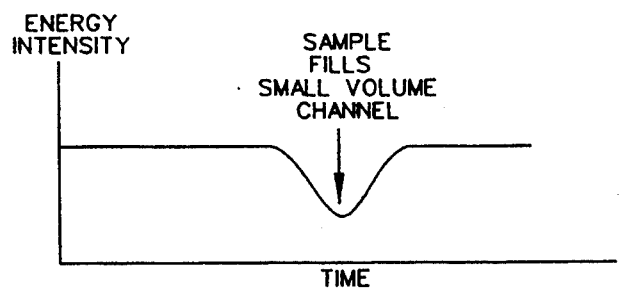
FIG. 4 demonstrates the characteristics of a typical energy intensity absorbtion plot provided by a spectrophotometer detector of the first embodiment of the present invention as a microliter/volume analyte containing sample is analyzed therein.

FIG. 4 shows a typical energy intensity absorbtion plot a detector (19) or (20) will provide as an analyte containing sample solution bolus passes through a small volume channel of the present invention. Said plot represents the energy intensity of electromagnetic wave beams (E3) or (E4) in FIG. 1, for instance.

Figure 3:
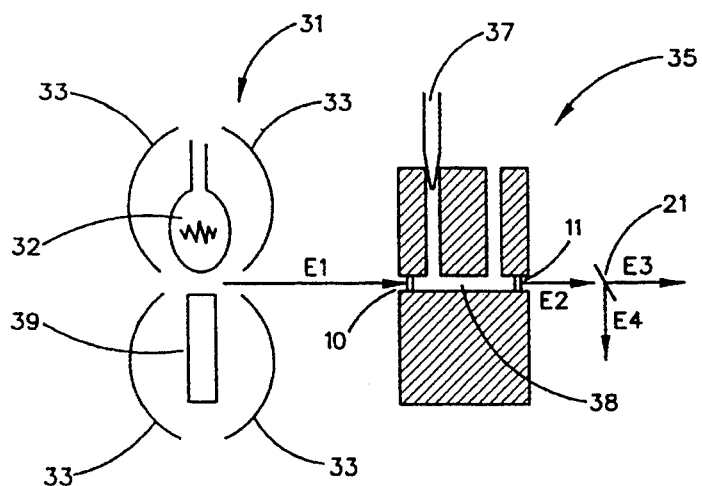
FIG. 3 shows a diagramatic view of a modified embodiment of the present invention utilizing a small volume channel containing cuvette for use in sample entry.

FIG. 3 shows a modified embodiment of the present invention. A typically small volume channel (38) containing cuvette (35) with means for entering a small volume analyte containing sample solution thereto, typically by means of a pipet (37) is shown. Said typically small volume channel (38) provides input (10) and output (11) apertures at the ends thereof which allow electromagnetic wave beams E1 and E2 to enter and exit, respectively, the typically small volume channel (38) during use when a small volume of analyte containing sample solution is present therein. Electromagnetic wave beam E2 is shown impinging on wave splitter (21) with a similar result being achieved as was described with respect to the first embodiment of the present invention above. Also shown in FIG. 3 is a source of multiple single wavelength electromagnetic waves (31). A bulb (32) is shown within reflectors (33). Multiple single wavelength electromagnetic waves emitted by bulb (32) are guided by reflectors (33) into contact with phosphor plate (39). Phosphor plate (39) provides electromagnetic wave beam E1, which typically contains multiple, phosphor specific, single wavelength electromagnetic waves, such as two-hundred-sixty (260) and two-hundred-eighty (280) nanometers, for instance. The major difference between the first and the modified embodiments is that the first utilizes one or more small volume channel containing flow cells to facilitate sample solution entry, and the modified embodiment utilizes a typically small volume channel containing cuvette. As well, the modified embodiment is shown as utilizing a phosphor plate (39). It is to be understood, however, that the source of electromagnetic waves (9) shown in FIG. 1, and (39) shown in FIG. 3 can be exchanged. That is a phosphor plate could be utilized in the first embodiment, and the source of multiple single wavelength electromagnetic wave beams shown in FIGS. 1 and 2 could be applied to the modified embodiment of the present invention system shown in FIG. 3.

Figure 5:
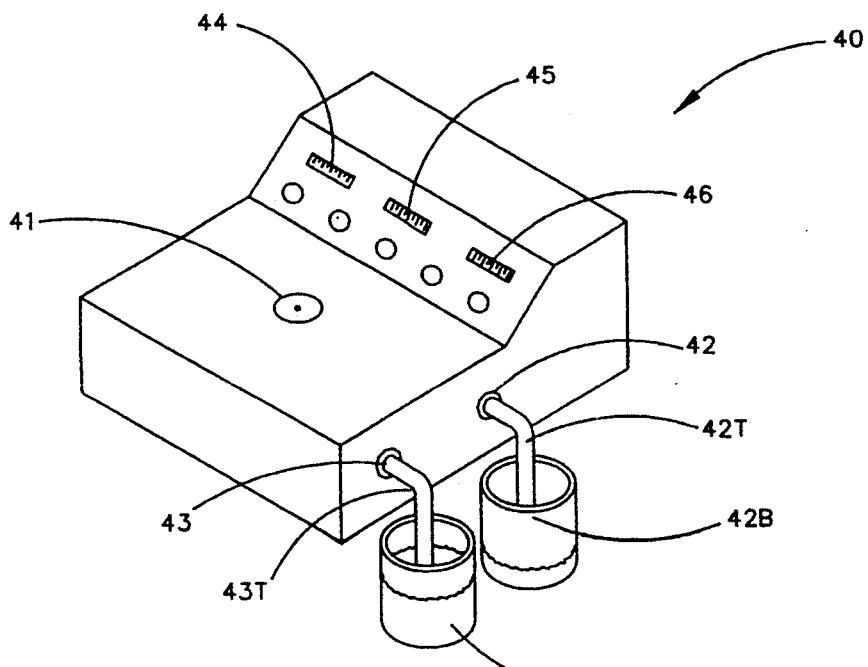
FIG. 5 shows a perspective view of a desk top sized housing for the first embodiment of the present invention.

FIG. 5 shows a typical desk top size housing (40), (eg. twelve (12) inches on a side and six (6) inches high), for the first embodiment of the present invention. Note the presence of carrier fluid input and output ports (43) and (42) respectively. Tubing (43T) and (42T) is shown entering desk top size housing (40) and providing access to source (43B) and sink (42B) for carrier fluid flow (F). Also shown are various display devices (44), (45), and (46). Said display devices might provide a user instantaneous information regarding energy absorbtion factors for multiple single wavelength electromagnetic wave beams, as well as ratios of more than one such energy absorbtion factor. Said display devices shown at& exemplary and more display devices might be present as might means for recording absorbtion data in memory devices such as hard or floppy disks. Carrier fluid pumping means and electromagnetic wave beam energy absorbtion analysis electronics are housed inside the desk top size housing (40). A housing for the modified embodiment will be of a similar design, but with the carrier fluid input and output ports deleted and with the sample analyte containing solution entry means appropriately modified.

The present invention is then found primarily in the described conveniently sized spectralphotometric systems, and in the method of applying a beam comprised of multiple single wavelength electromagnetic waves to an analyte containing sample solution, in conjunction with the simultaneous determination, displaying and/or recording of energy absorbtion factors associated with multiple single wavelength electromagnetic waves, and ratios thereof, as said multiple single wavelength electromagnetic beam is caused to pass through an analyte containing sample solutions. In that light it is to be understood that, in combination with other aspects of the present invention, the beam splitter (21) is considered to be a particularly important aspect, as it is said beam splitter which serves to provide a multiplicity of electromagnetic wave beams, during use. Said multiple electromagnetic wave beams being simultaneously, instantaneously and conveniently subjected to independent analysis regarding energy absorbtion factors for single wavelength electromagnetic waves in each of said multiple electromagnetic wave beams.

Finally, while the present disclosure identifies application to microliter volume sample solutions as an appropriate application of the present invention, the scope of the present invention includes application to larger volume sample solutions.

Having hereby disclosed the subject matter of this invention, it should be obvious that many modifications and substitutions and variations of the present invention are possible in light of the teachings. It is therefore to be understood that the invention may be practiced other than as specifically described, and should be limited in breadth and scope only by the claims.

I claim:

1. A system for detecting and quantifying the amount of one or more analytes in a sample analyte containing sample solution comprising:

one or more sample flow cells each with a channel present therethrough;

means for providing a continuous flow of carrier fluid through each channel in said one or more sample flow cells;

means to introduce a sample analyte containing sample solution into one said channel in the one or more sample flow cells, in the form of a bolus in the continuous flow of carrier fluid;

phosphor plate means to produce and cause a beam comprised of two or more single wavelength electromagnetic waves to pass through said bolus of sample analyte containing sample solution as it is caused to pass through one said channel in said one or more sample flow cells; and means to simultaneously detect, display and optionally record the amounts of energy absorbed from two or more selected single wavelength electromagnetic waves in the beam of two or more single wavelength electromagnetic waves, as said beam is passed through the bolus of sample analyte containing sample solution as it passes through said one channel in said one or more sample flow cells;

the magnitude of which energy absorbed from each selected single wavelength electromagnetic wave being proportional to the quantity of an analyte, or analytes, in the bolus of sample analyte containing sample solution.

2. A system for detecting and quantifying the amount of one or more analytes as in claim 1, in which the volume of the sample analyte containing sample solution bolus is equal to, or greater than, the internal volume of the channel in said one of said one or more sample flow cells, which is on the order of a few microliters or less.

3. A system for detecting and quantifying the amount of one or more analytes as in claim 1, which further comprises means to determine and display ratios of the amount of energy absorbed from more than one single wavelength electromagnetic wave which are, simultaneously, passed through the sample analyte containing sample solution bolus as it passes through the channel in said one of said one or more sample flow cells.

4. A system for detecting and quantifying the amount of one or more analytes as in claim 1, in which the means for providing the continuous flow of carrier fluid is a pump.

5. A system for detecting and quantifying the amount of one or more analytes as in claim 1, in which the carrier fluid of the continuous flow of carrier fluid is water.

6. A system for detecting and quantifying the amount of one or more analytes as in claim 1, in which the carrier fluid of the continuous flow of carrier fluid is the same as the solvent in the sample analyte containing sample solution.

7. A system for detecting and quantifying the amount of one or more analytes as in claim 1, in which the carrier fluid of the continuous flow of carrier fluid is other than water or the solvent in the sample analyte containing sample solution.

8. A system for detecting and quantifying the amount of one or more analytes as in claim 1, which is housed in an encasement of a size suitable for use on the top of a desk.

9. A system for detecting and quantifying the amount of one or more analytes in a sample analyte containing sample solution as in claim 1, in which the means to simultaneously detect, display and optionally record the amount of energy absorbed from two or more selected single wavelength electromagnetic waves in the beam comprised of two or more single wavelength electromagnetic waves, as said beam is passed through the bolus of sample analyte containing sample solution as it passes through said one channel in said one or more sample flow cells comprises a beam splitter which receives a beam of electromagnetic waves comprised of two or more single wavelength electromagnetic waves, and provides two beams of electromagnetic waves, each being simultaneously directed into a separate spectrophotometric detector.

10. A system for detecting and quantifying the amount of one or more analytes as in claim 1, in which the means for the sample analyte containing solution to the continuous flow of carrier fluid is a needle and hypodermic syringes system with an internal volume on the order of ten (10) microliters, the needle of which needle and hypodermic syringe system injects the sample analyte containing sample solution into the continuous flow of carrier fluid in the form of a bolus, at a position in the continuous flow of carrier fluid ahead of the channel in one of said one or more sample flow cells.

11. A system for detecting and quantifying the amount of one or more analytes as in claim 10, in which the needle of the needle and hypodermic syringe system gains access to the continuous flow of carrier fluid by piercing and projecting through a septum, which septum otherwise presents a continuous barrier which separates the channel in one of said one or more sample flow cells from the surrounding environment.

12. A system for detecting and quantifying the amount of one or more analytes as in claim 11, in which the septum is of a self resealing type such that after the needle of the needle and hypodermic syringe system is removed therefrom, said self resealing septum again forms a continuous barrier between the channel in one of said one or more sample flow cells and the external environment.

13. A system for detecting and quantifying the amount of one or more analytes in sample analyte containing sample solution comprising:
a cuvette with a channel therethrough;
means to introduce a sample analyte containing sample solution into the channel;
phosphor plate means to produce and cause a beam comprised of two or more single wavelength electromagnetic waves to pass through said sample analyte containing sample solution caused to be present in the channel of said cuvette; and
means to simultaneously detect, determine, display and optionally record the amounts of energy absorbed from two or more selected single wavelength electromagnetic waves in the beam of two or more single wavelength electromagnetic waves passed through the sample analyte containing sample solution in the channel of the cuvette;
the magnitude of which energy absorbed from each selected single wavelength electromagnetic wave being proportional to the quantity of an analyte, or analytes, in the sample analyte containing sample solution.

14. A system for detecting and quantifying the amount of one or more analytes as in claim 13, in which the volume of the sample analyte containing sample solution is equal to, or greater than, that of the channel the cuvette, which is on the order of a few microliters or less.

15. A system for detecting and quantifying the amount of one or more analytes as in claim 13, which further comprises means to determine and display ratios of the amount of energy absorbed from more than one single wavelength electromagnetic wave which are, simultaneously, passed through the sample analyte containing sample solution present in the channel of said cuvette.

16. A system for detecting and quantifying the amount of one or more analytes as in claim 13, in which the means to introduce a sample analyte containing sample solution to the channel in the cuvette is a pipet.

17. A system for detecting and quantifying the amount of one or more analytes as in claim 13, which is housed in an encasement of a size suitable for use on the top of a desk.

18. A system for detecting and quantifying the amount of one or more analytes in a sample analyte containing sample solution as in claim 13, in which the means to simultaneously detect, display and optionally record the amounts of energy absorbed from two or more selected single wavelength electromagnetic waves in the beam comprised of two or more single wavelength electromagnetic waves, as said beam is passed through the sample analyte containing sample solution resting in the channel of the cuvette, comprises a beam splitter which receives a beam of electromagnetic waves comprised of two or more single wavelength electromagnetic waves, and provides two beams of electromagnetic waves, each being simultaneously directed into a separate spectrophotometric detector.

19. A method of detecting and quantifying the amount of one or more analytes in a sample solution comprising the steps of:
   a. obtaining a system for detecting and quantifying the amount of one or more analytes in a sample analyte containing sample solution comprising:
      one or more sample flow cells each with a channel present therethrough;
      means for providing a continuous flow of carrier fluid through each channel in said one or more sample flow cells;
      means to introduce a sample analyte containing sample solution into one said channel in the one or more sample flow cells, in the form of a bolus in the continuous flow of carrier fluid;
      phosphor plate means to produce and cause a beam comprised of two or more single wavelength electromagnetic waves to pass through said bolus of sample analyte containing sample solution as it is caused to pass through said one said channel in said one or more sample flow cells; and
      means to simultaneously detect, display and optionally record the amount of energy absorbed from two or more selected single wavelength electromagnetic waves in the beam of two or more single wavelength electromagnetic waves, as said beam is passed through the bolus of sample analyte containing sample solution as it passes through one said channel in said one or more sample flow cells;
      the magnitude of which energy absorbed from each selected single wavelength electromagnetic wave being proportional to the quantity of an analyte, or analytes, in the bolus of sample analyte containing sample solution;
   b. causing a continuous flow of carrier fluid through the each channel in said one or more sample flow cells;
   c. entering a bolus of analyte containing sample solution into the continuous flow of carrier fluid ahead of said one said channel of said one or more sample flow cells so that it flows thereinto;
   d. producing and simultaneously causing, with said phosphor plate means, two or more single wavelength electromagnetic waves in a beam comprised of electromagnetic waves to pass through the bolus of analyte containing sample solution;
   e. detecting the amount of energy absorbed from the each of the two or more single wavelength electromagnetic waves in the beam comprised of electromagnetic waves as they pass through said bolus of analyte containing sample solution;
   f. displaying and optionally recording simultaneous multiple single wavelength electromagnetic wave energy absorbtion values; and
   g. analyzing said energy absorbtion values to determine the quantities of analyte(s) present in the analyte containing sample solution.

20. A method of detecting and quantifying the amount of one or more analytes in a sample solution comprising the steps of:
   a. obtaining a system for detecting and quantifying the amount of one or more analytes in a sample analyte containing sample solution comprising:
      a cuvette with a channel therethrough;
      means to introduce a sample analyte containing sample solution into said channel;
      phosphor plate means to produce and cause a beam comprised of two or more single wavelength electromagnetic waves to pass through said sample analyte containing sample solution in the channel of said cuvette; and
      means to simultaneously determine, display and optionally record the amount of energy absorbed from two or more selected single wavelength electromagnetic waves in the beam of two or more single wavelength electromagnetic waves passed through the sample analyte containing sample solution in the channel of the cuvette;
      the magnitude of which energy absorbed from each selected single wavelength electromagnetic wave being proportional to the quantity of an analyte, or analytes, in the sample analyte containing sample solution;
   b. entering an analyte containing sample solution into the channel in the cuvette;
   c. producing and simultaneously causing, with said phosphor plate means, two or more single wavelength electromagnetic waves in a beam comprised of electromagnetic waves to pass through the sample solution present in said cuvette;
   d. detecting the amount of energy absorbed from the each of the two or more single wavelength electromagnetic waves in the beam of electromagnetic waves as they pass through said sample solution;
   e. displaying and optionally recording simultaneous multiple single wavelength electromagnetic wave energy absorbtion values; and
   f. analyzing said energy absorbtion values to determine the quantities of analyte(s) present in the analyte containing sample solution.

* * * * *